United States Patent [19]

Perronnet et al.

[11] 3,932,433
[45] Jan. 13, 1976

[54] PESTICIDAL PHOSPHOROUS-THIAZOLE COMPOUNDS

[75] Inventors: Jacques Perronnet, Paris; Laurent Taliani, Les Pavillons-sous-Bois, both of France

[73] Assignee: Roussel-UCLAF, Paris, France

[22] Filed: Dec. 26, 1974

[21] Appl. No.: 536,424

[30] Foreign Application Priority Data
Jan. 8, 1974  France.............................. 74.00536

[52] U.S. Cl............................ 260/302 E; 424/200
[51] Int. Cl.².......................................... C07D 277/60
[58] Field of Search................................ 260/302 G

[56] References Cited
UNITED STATES PATENTS 3,159,645  12/1964  Rigterink....................... 260/302 E
3,687,963  8/1972  Hoffmann et al. ............. 260/302 E

*Primary Examiner*—Raymond V. Rush
*Attorney, Agent, or Firm*—Hammond & Littell

[57] ABSTRACT

Thiazole derivatives of the formula

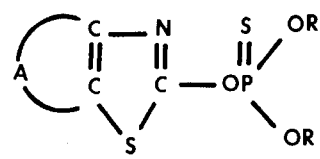

wherein A is alkylene of 3 to 5 carbon atoms optionally substituted with a member of the group consisting of =O and

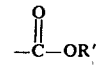

wherein R' is alkyl of 1 to 5 carbon atoms and R is alkyl of 2 to 3 carbon atoms having insecticidal and/or acaricidal properties and their preparation.

8 Claims, No Drawings

PESTICIDAL PHOSPHOROUS-THIAZOLE COMPOUNDS

OBJECTS OF THE INVENTION

It is an object of the invention to provide the novel thiazole derivatives of formula I and a novel process for their preparation.

It is another object of the invention to provide novel insecticidal and/or acaricidal compositions as well as to provide a novel method for killing insects and/or acariens.

These and other objects and advantages of the invention will become obvious from the following detailed description.

THE INVENTION

The novel thiazole compounds of the invention have the formula

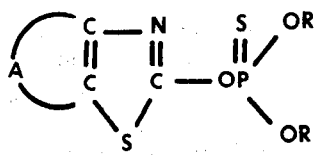

I wherein A is alkylene of 3 to 5 carbon atoms optionally substituted with a member of the group consisting of =O and

wherein R' is alkyl of 1 to 5 carbon atoms and R is alkyl of 2 to 3 carbon atoms.

Among the preferred compounds of formula I are 2-(diethoxythiophosphoryloxy)-4,5,6,7-tetrahydrobenzothiazole, 2-(diethoxythiophosphoryloxy)-4,5,6,7-tetrahydro-7-oxo-benzothiazole, 2-(diethoxythiophosphoryloxy)-5,6,7,8-tetrahydro -4H-cycloheptathiazole, 2-(diethoxythiophosphoryloxy)-5,6-dihydro-4H-cyclopentathiazole, 2-(diethoxythiophosphoryloxy)-4-carbomethoxy-4,5,6,7-tetrahydrobenzothiazole, 2-(diethoxythiophosphoryloxy)-4-carbethoxy-4,5,6,7-tetrahydrobenzothiazole, 2-(diethoxythiophosphoryloxy)-4-carbo-n-propoxy-4,5,6,7-tetrahydrobenzothiazole and the corresponding dipropoxy- and diisopropoxy-thiophosphoryloxy derivatives.

The novel process of the invention for the preparation of the compounds of formula I comprises reacting in the presence of a basic agent a compound of the formula

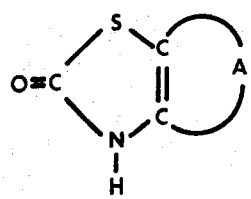

II with a chlorothiophosphate of the formula

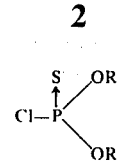

wherein A and R have the above definition. The basic agent may be an alkali metal carbonate or hydride such as sodium hydride and potassium carbonate and a tertiary amine such as triethylamine. The reaction is preferably effected in an organic solvent such as acetone, acetonitrile, dimethylformamide or tetrahydrofuran.

The compounds of formula II may be prepared by condensing a compound of the formula

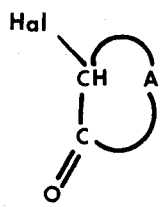

with an alkyl thiocarbamate. Stevens et al [JACS, Vol. 79 (1957), p. 5263] describes 2,3,4,5,6,7-hexahydrobenzothiazoline-2-one,2,3,5,6-tetrahydro-4H-cyclopentathiazoline-2-one and 2,3,5,6,7,8-hexahydro-4H-cycloheptathiazoline-2-one.

The novel insecticidal and/or acaricidal compositions of the invention are comprised of an effective amount of at least one compound of formula I and a carrier. The compositions may be in the form of powders, granules, emulsions, suspensions or solutions containing one or more of the active agents. The compositions may also contain non-ionic, anionic and cationic surface active agents; an inert powder such as talc, clays, silicates and kieselguhr; and/or a vehicle such as water, alcohol, hydrocarbons or other organic solvents or animal, vegetable or mineral oils.

Liquid insecticidal compositions used for foliar spraying preferably contain 10 to 80% by weight of a compound of formula I and the acaricidal liquids for foliar spraying preferably contain 20 to 80% by weight of the compound of formula I.

Tests with the compositions have shown them to be effective against insects such as Drosophila melanogaster, Blattella germanica, Sitophilus granarius, Musca domestica, Spodoptera littoralis caterpillars and Musca domestica larvae and against acariens such as Tetranychus urticae.

The novel method of the invention for killing insects and/or acariens comprises contacting insects and/or acariens with a lethal amount of at least one compound of formula I.

In the following examples there are described several preferred embodiments to illustrate the invention. However, it is to be understood that the invention is not intended to be limited to the specific embodiments.

EXAMPLE 1

2-(diethoxythiophosphoryloxy)-4,5,6,7-tetrahydrobenzothiazole

A mixture of 6.2 g of 2,3,4,5,6,7-hexahydrobenzothiazoline-2-one, 8.4 g of potassium carbonate and 300 ml of acetone was refluxed for 1 hour and after the addition of 11.4 g of 0,0-diethyl chlorothiophosphate thereto, the mixture was refluxed for another hour. The mixture was stirred at room temperature for 24 hours and was filtered to remove mineral salts. The filtrate was concentrated to dryness by distillation under reduced pressure and the residue was chromatographed over silica gel. Elution with an 8-2 cyclohexaneethyl acetate mixture yielded 7.3 g of 2-(diethoxythiophosphoryloxy)-4,5,6,7-tetrahydrobenzothiazole having a refractive index of $n_D^{22} = 1.532$ Analysis: $C_{11}H_{18}NO_3PS_2$ Calculated: %C 43.00; %H 5.91; %N 4.56; %P 10.08. Found: 43.3; 5.9; 4.4; 9.8.

EXAMPLE 2

2-(diethoxythiophosphoryloxy)-4,5,6,7-tetrahydro-7-oxo-benzothiazole

STEP A: 7-oxo-2,3,4,5,6,7-hexahydrobenzothiazoline-2-one

A mixture of 29.3 g of 2-chloro-1,3-cyclohexanedione [Muehlstaedt et al, J. Prakt Chem., Vol. 20 (1963), p. 285] and 21 g of ethyl thiocarbamate was heated at 140°C for 15 minutes and was then poured into water. The precipitate formed was recovered by vacuum filtering and was crystallized from isopropyl alcohol to obtain 12.2 g of 7-oxo-2,3,4,5,6,7-hexahydrobenzothiazoline-2-one melting at 262°C.

Analysis: $C_7H_7NO_2S$ Calculated: % C 49.69; %H 4.17; %N 8.28; % S 18.95. Found: 49.7; 4.1; 8.0; 19.0.

STEP B: 2-(diethoxythiophosphoryloxy)-4,5,6,7-tetrahydro-7-oxo-benzothiazole

A mixture of 8.4 g of 7-oxo-2,3,4,5,6,7-hexahydrobenzothizaoline-2-one, 10.5 g of potassium carbonate and 100 ml of acetone was refluxed for 1 hour and after addition of 14.5 g of 0,0-diethyl chlorothiophosphate thereto, the mixture was refluxed for another hour. The mixture was stirred at room temperature for 24 hours and the mineral salts formed were filtered off. The filtrate was distilled to dryness under reduced pressure and the residue was chromatographed over silica gel. Elution with a 6-4 cyclohexane-ethyl acetate mixture resulted in 3.5 g of 2-(diethoxythiophosphoryloxy)-4,5,6,7-tetrahydro-7-oxo-benzothiazole with a refractive index of $n_D^{20} = 1.555$ Analysis: $C_{11}H_{16}NO_4PS_2$ Calculated: % C 41.11; % H 5.02; % N 4.36; %P 9.64. Found: 41.5; 5.0; 4.1; 9.7.

EXAMPLE 3

2-(diethoxythiophosphoryloxy)-5,6,7,8-tetrahydro-4H-cyclo-heptathiazole.

A mixture of 8.5 g of 2,3,5,6,7,8-hexahydro-4H-cycloheptathiazoline-2-one, 7 g of potassium carbonate and 200 ml of acetone was refluxed for 1 hour and after addition of 9.5 g of 0,0-diethyl chlorothiophosphate thereto, the mixture was refluxed 24 hours. The mixture was filtered to remove mineral salts and the filtrate was distilled to dryness under reduced pressure. The residue was chromatographed over silica gel and elution with an 8-2 cyclohexane-ethyl acetate mixture gave 6 g of 2-(diethoxythiophosphoryloxy)-5,6,7,8-tetrahydro-4H-cycloheptathiazole with a refractive index of $n_D^{19} = 1.5246$ Analysis: $C_{12}H_{20}NO_3PS_2$ Calculated: % C 44.85; % H 6.28; % N 4.36; % P 9.64. Found: 45.1; 6.4; 4.4; 9.6.

EXAMPLE 4

2-(diethoxythiophosphoryloxy)-5,6-dihydro-4H-cyclopentathiazole

A mixture of 21 g of 2,3,5,6,-tetrahydro-4H-cyclopentathiazoline-2-one, 21 g of potassium carbonate and 300 ml of acetone was refluxed for 1 hour and after the addition of 28 g of 0,0-diethyl chlorothiophosphate thereto, the mixture was refluxed for 1 hour. The mineral salts were filtered off and the filtrate was distilled to dryness under reduced pressure. The residue was chromatographed over silica gel and was eluted with an 8-2 cyclohexane-ethyl acetate to obtain 4g of 2-(diethoxythiophosphoryloxy)-5,6-dihydro-4H-cyclopentathiazole with a refractive index of $n_D^{28} = 1.5348$ Analysis: $C_{10}H_{16}NO_3PS_2$ Calculated: % C 40.93; %H 5.50; % N 4.77; % P 10.56. Found: 40.9; 5.5; 4.7; 10.4.

EXAMPLE 5

2-(diethoxythiophosphoryloxy)-4-carbomethoxy-4,5,6,7-tetrahydrobenzothiazole

STEP A: 4-carbomethoxy-2,3,4,5,6,7-hexahydrobenzothiazoline-2-one

A mixture of 10.5 g of ethyl thiocarbamate, 25.9 g of methyl 3-bromo-2-oxo-cyclohexanecarboxylate and 200 ml of dioxane was refluxed for 16 hours and was then distilled to dryness under reduced pressure. The residue was chromatographed over silica gel and was eluted with a 1-1 cyclohexane-ethyl acetate mixture to obtain 4-carbomethoxy-2,3,4,5,6,7-hexahydrobenzothiazoline-2-one melting at 95°C.

Analysis: $C_9H_{11}NO_3S$ Calculated: % C 50.71; % H 5.20; % N 6.57. Found: 50.4; 5.2; 6.4.

STEP B: 2-(diethoxythiophosphoryloxy)-4-carbomethoxy-4,5,6,7-tetrahydrobenzothiazole A mixture of 4 g of 4-carbomethoxy-2,3,4,5,6,7-hexahydrobenzothiazoline-2-one, 3 g of potassium carbamate and 50 ml of acetone was refluxed for 1 hour and after the addition of 4 g of 0,0-diethyl chlorothiophosphate, the mixture was refluxed for another hour. The mixture was stirred for 18 hours at room temperature and the mineral salts formed were filtered off. The filtrate was distilled to dryness under reduced pressure and the residue was chomatographed over silica gel. Elution with an 8-2 cyclohexane-ethyl acetate mixture yielded 1.5 g of 2-(diethoxythiophosphoryloxy)-4-carbomethoxy-4,5,6,7-tetrahydrobenzothiazole with a refractive index $n_D^{26} = 1.5261$ Analysis: $C_{13}H_{20}NO_5PS_2$ Calculated: % C 42.73; % H 5.52; % N 3.84; %P 8.48. Found: 43.0; 5.7; 4.1; 8.4.

EXAMPLE 6

2-(diethoxythiophosphoryloxy)-4-carbethoxy-4,5,6,7-tetrahydrobenzothiazole

STEP A: 4-carbethoxy-2,3,4,5,6,7-hexahydrobenzothiazoline-2-one

Using the procedure of Step A of Example 5, ethyl 3-bromo-2-oxo-cyclohexanecarboxylate was reacted to obtain 4-carbethoxy-2,3,4,5,6,7-hexahydrobenzothiazoline-2-one melting at 84°C.

Analysis: $C_{10}H_{13}NO_3S$ Calculated: % C 52.87; % H 5.76; % N 6.16; % S 14.11. Found: 52.6; 5.8; 6.1; 14.2.

STEP B: 2-(diethoxythiophosphoryloxy)-4-carbethoxy-4,5,6,7-tetrahydro-benzothiazole Using the procedure of Step B of Example 5, 7.6 g of 4-carbethoxy-2,3,4,5,6,7-hexahydrobenzothiazoline-2-one were reacted to obtain 7.5 g of 2-(diethoxythiophosphoryloxy)-4-carbethoxy-4,5,6,7-tetrahydrobenzothiazole with a refractive index of $n_D^{19.5} = 1.5206$ Analysis: $C_{14}H_{22}NO_5PS_2$ Calculated: % C 44.31; %H 5.85; % N 3.7; % P 8.16. Found: 44.15; 5.9; 3.4; 8.3.

EXAMPLE 7

2-(diethoxythiophosphoryloxy)-4-carbo-n-propoxy-4,5,6,7-tetrahydrobenzothiazole

STEP A: 4-carboxy-2,3,4,5,6,7-hexahydrobenzothiazoline-2-one

A mixture of 6.8 g of 4-carbethoxy-2,3,4,5,6,7-hexahydrobenzothiazoline-2-one and 6 ml of 10 N sodium hydroxide in 100 ml of water was refluxed for 3 hours and then cooled to 20°C. 6 ml of 10 N hydrochloric acid were added thereto and the mixture was vacuum filtered. The precipiate was washed with acetone and 1 g of the raw product was taken up in a solution of 0.42 g of sodium bicarbonate in 40 ml of water. The mixture was stirred for 1 hour, was washed with ethyl acetate and was acidified with 1 N hydrochloric acid. The mixture was vacuum filtered and the precipitate was washed with water and dried to obtain 0.5 g of 4-carboxy-2,3,4,5,6,7-hexahydrobenzothiazole-2-one melting at 192°C.

STEP B: 4-(carbo-n-propoxy)-2,3,4,5,6,7-hexahydrobenzothiazoline-2-one

A mixture of 29 g of the product of Step A, 7.83 g of sodium bicarbonate and 250 ml of methanol was stirred for 45 minutes at 20°C and the solvent was then evaporated. 400 ml of propanol and 15.73 g of ethyl chloroformate were added to the mixture which was stirred for 48 hours at 20°C and then 2 hours at reflux. The mixture was iced and filtered and the filtrate was evaporated to dryness. The oil was taken up in ethyl acetate and the organic phase was washed with water, dried and evaporated to dryness. The residue was taken up in hot isopropyl ether which was cooled and vacuum filtered to obtain 12 g of crystals of 4-(carbo-n-propoxy)-2,3,4,5,6,7-hexahydrobenzothiazoline-2-one melting at 85°C.

Analysis: $C_{11}H_{15}NO_3S$ Calculated: % C 54.75; % H 6.26; % N 5.80; % S 13.28. Found: 54.6; 6.4; 5.6; 13.2.

STEP C: 2-(diethoxythiophosphoryloxy)-4-carbo-n-propoxy-4,5,6,7-tetrahydrobenzothiazole A mixture of 8 g of 4-carbo-n-propoxy-2,3,4,5,6,7-hexahydrobenzothiazoline-2-one, 250 ml of acetone and 5.52 g of potassium carbonate was refluxed for 2 hours and after the addition of 7.54 g of 0,0-diethyl chlorothiophosphate thereto, the mixture was refluxed for 20 hours and then was filtered. The filtrate was evaporated to dryness and the residue was chromatographed over silica gel. Elution with a 7-3 cyclohexane-ethyl acetate mixture yielded 11.5 g of 2-(diethoxythiophosphoryloxy)-4-carbo-n-propoxy-4,5,6,7-tetrahydrobenzothiazole with a refractive index of $n_D^{20} = 1.5190$ Analysis: $C_{15}H_{24}NO_5PS_2$ Calculated: % C 45.78; % H 6.14; % N 3.55; % P 7.87. Found: 45.8; 6.2; 3.5; 7.7.

TEST DATA

The insecticidal and acaricidal activity was determined for 2-(diethoxythiophosphoryloxy)-4,5,6,7-tetrahydrobenzothiazole (compound A) and 2-(diethoxythiophosphoryloxy)-4-carbethoxy-4,5,6,7-tetrahydrobenzothiazole (compound B).

A. *Drosophila melanogaster*

This test measured the activity of the vapors of the product and consisted of placing the insects in a Petri dish 10 cm in diameter joined by a tergal screen to a crystallizer of the same diameter in which the test product was placed in acetone solution. The solvent was evaporated before the insects were introduced and 3 tests per concentration and 25 insects per test were run. The insects were less than 48 hours old adults and the percent mortality was determined after 1.4 and 6 hours and the results are reported in Table I.

TABLE I

| Compound | Concentrations in ppm | 500 | 50 | 5 |
|---|---|---|---|---|
| A | 1 hour | 0 | 0 | 0 |
|   | 4 hours | 100 | 100 | 66 |
|   | 6 hours | 100 | 100 | 100 |

B. *Male Blatella germanica*

This test was effected by topical application with adult male Blattes germanica receiving 2 microliters of an acetone solution of the test product between the second and third pair of feet. After the treatment, the test insects were held in a dim light at 20°C and were fed. Readings were made 24 and 48 hours and 6 days after treatment. The results of Table II are expressed as percent of mortality.

TABLE II

| Compound | Concentration in ppm | 5000 | 1250 | 625 | 312.5 |
|---|---|---|---|---|---|
| A | 24 hrs. | — | 90 | 0 | 0 |
|   | 48 hrs. | — | 90 | 0 | 0 |
|   | 6 days | — | 100 | 37 | 0 |
| B | 24 hrs. | 100 | 55 | — | — |
|   | 48 hrs. | 100 | 80 | — | — |
|   | 6 days | 100 | 90 | — | — |

C. *Sitophilus granarius*

0.2 μl of an acetone solution of the test compound was applied to the ventral thorax of each insect with 50 insects for each concentration of 5000, 500 and 50 ppm.

The readings were made 4 and 24 hours and 5 days after treatment. The results in Table III were expressed as the percent of mortality.

TABLE III

| Compound | Concentration in ppm | 5000 | 500 | 50 |
|---|---|---|---|---|
| A | 4 hrs. | 100 | 100 | 100 |
|   | 24 hrs. | 100 | 100 | 88 |
|   | 5 days | 100 | 100 | 92 |
| B | 4 hrs. | 100 | 100 | — |
|   | 24 hrs. | 100 | 100 | — |
|   | 5 days | 100 | 100 | — |

D. *Musca domestica*

This test was a topical application to flies which received one microliter of an acetone solution of the product applied to the dorsal thorax having been put to sleep with ether. The insects were held at 20°C and a 50% relative humidity. They were fed with milk or water and readings of percent mortality were taken 1 hour and 24 hours after treatment and the results are reported in Table IV.

TABLE IV

| Compound | Concentration in ppm | 5000 | 2500 | 500 |
|---|---|---|---|---|
| A | 1 hr. | 100 | 100 | 53 |
|   | 24 hrs. | 100 | 100 | 57 |
| B | 1 hr. | 94 | 100 | 70 |
|   | 24 hrs. | 100 | 100 | 100 |

E. Spodoptera littoralis

Spodoptera littoralis caterpillars about 1 to 1.5 cm long and about 10 days old were fed treated leaves using 15 caterpillars for each test. Rings of lettuce 8 mm in diameter received 4 ml of an acetone solution of the test product and were placed in a plastic closed dish 5 cm in diameter. The caterpillars were held in the dishes at 20°C and 50% relative humidity and are maintained until they had eaten the treated leaf. Readings of the percent of mortality were taken 1 hour, 24 hours and 48 hours and/or 8 days after the treatment and the results are reported in Table V.

TABLE V

| Product | Readings after | Concentration in ppm | | | |
|---|---|---|---|---|---|
|   |   | 5000 | 500 | 250 | 125 |
| A | 1 hr. | — | 0 | 0 | 0 |
|   | 24 hrs. | — | 90 | 90 | 40 |
|   | 48 hrs. | — | 100 | 100 | 70 |
| B | 48 hrs. | 80 | 60 | — | — |
|   | 8 days | 95 | 88 | — | — |

F. Musca domestica larvae

This contact-ingestion test consisted of placing 2 ml of an acetone solution of varying concentrations of the test compound with 1 g of bran placed in a watch glass and the solvent was evaporated. Then the treated bran was placed in a plastic container and 2 ml of milk were added thereto. After a good mixing, the bran was contaminated with 20 Musca domestica larvae aged 3 to 4 days. 3 tests were run for each concentration and the larvae were held at 20°C and 30% relative humidity. Readings expressed as percent of mortality were taken 48 hours and 8 days after treatment and the results are reported in Table VI.

TABLE VI

| Product | Readings after | Concentration in ppm | |
|---|---|---|---|
|   |   | 5000 | 500 |
| A | 48 hrs. | 80 | 60 |
|   | 8 days | 95 | 88 |
| B | 48 hrs. | 97 | 95 |
|   | 8 days | 100 | 100 |

The results of Tests A to F demonstrate that the two compounds, A and B, have interesting insecticidal properties.

G. Acaricidal Activity

Bean leaves infested with Tetranychus urticae were divided into 2 groups with 1 group being sprayed with 0.5 ml of an aqueous solution of compound A per leaf with concentrations of 50, 10 and 1 mg of compound A per liter. After drying the leaves were contaminated with a population of 20 to 25 adult acariens. The second control group of leaves were untreated and the number of acariens living 48 hours after treatment was determined. The results were expressed as the percentage of reduction of living acariens on the treated leaves as compared to the control leaves. 9 days after treatment, the dead larvae and unhatched eggs were also counted and the results are reported in Table VII.

TABLE VII

| Compound | Concentration in mg/l | % mortality | | |
|---|---|---|---|---|
|   |   | adults | eggs | larvae |
| A | 50 | 100 | 100 | 100 |
|   | 10 | 98.0 | 21.7 | 76.2 |
|   | 1 | 17.8 | 16.9 | 45.2 |

Table VII shows that compound A possesses good acaricidal activity against Tetranychus urticae.

COMPOSITION A

A composition useful for insecticidal or acaricidal activity consisted of 15% by weight of 2-(diethoxythiophosphoryloxy)-4,5,6,7-tetrahydrobenzothiazol, 6.4% by weight of Atlox 4851 (oxyethylene triglyceride with a sulfonate - Acid index: 1.5), 3.2% by weight of Atlox 4855 (oxyethylene triglyceride with a sulfonate - Acid index : 3) and 75.4% by weight of Xylene.

Various modifications of the compositions and methods of the invention may be made without departing from the spirit or scope thereof and it is to be understood that the invention is to be limited only as defined in the appended claims.

We claim:
1. A compound of the formula

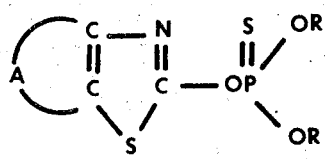

wherein A is polymethylene of 3 to 5 carbon atoms optionally substituted with a member of the group consisting of =O and

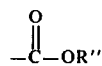

wherein R' is alkyl of 1 to 5 carbon atoms and R is alkyl of 2 to 3 carbon atoms.

2. A compound of claim 1 which is 2-(diethoxythiophosphoryloxy)-4,5,6,7-tetrahydrobenzothiazole.

3. A compound of claim 1 which is 2-(diethoxythiophosphoryloxy)-4,5,6,7-tetrahydro-7-oxo-benzothiazole.

4. A compound of claim 1 which is 2-(diethoxythiophosphoryloxy)-5,6,7,8-tetrahydro-4H-cycloheptathiazole.

5. A compound of claim 1 which is 2-(diethoxythiophosphoryloxy)-5,6-dihydro-4H-cyclopentathiazole.

6. A compound of claim 1 which is 2-(diethoxythiophosphoryloxy)-4-carbomethoxy-4,5,6,7-tetrahydrobenzothiazole.

7. A compound of claim 1 which is 2-(diethoxythiophosphoryloxy)-4-carbethoxy-4,5,6,7-tetrahydrobenzothiazole.

8. A compound of claim 1 which is 2-(diethoxythiophosphoryloxy)-4-carbo-n-propoxy-4,5,6,7-tetrahydrobenzothiazole.

* * * * *